US010525195B1

(12) United States Patent
Nuzzo et al.

(10) Patent No.: US 10,525,195 B1
(45) Date of Patent: Jan. 7, 2020

(54) INJECTION DEVICE (71) Applicant: RiteDose LLC, Woodbury, TN (US)

(72) Inventors: Thomas Nuzzo, San Francisco, CA (US); Justin M Hollar, Livermore, CA (US)

(73) Assignee: RiteDose, LLC, Woodbury, TN (US)

( * ) Notice: Subject to any disclaimer, the term of this patent is extended or adjusted under 35 U.S.C. 154(b) by 0 days.

(21) Appl. No.: 16/199,140

(22) Filed: Nov. 24, 2018

(51) Int. Cl.
*A61M 5/145* (2006.01)
*A61M 5/315* (2006.01)
*A61M 5/31* (2006.01)

(52) U.S. Cl.
CPC ........ *A61M 5/1458* (2013.01); *A61M 5/3137* (2013.01); *A61M 5/31585* (2013.01); *A61M 2005/14506* (2013.01); *A61M 2205/50* (2013.01); *A61M 2205/502* (2013.01); *A61M 2205/52* (2013.01)

(58) Field of Classification Search
CPC .............. A61M 5/1458; A61M 5/3137; A61M 5/31585; A61M 2005/14506; A61M 2205/50; A61M 2205/502; A61M 2205/52; A61M 2005/3152; A61M 5/482
See application file for complete search history.

(56) References Cited

U.S. PATENT DOCUMENTS

| 3,790,048 | A | 2/1974 | Luciano et al. |
| 4,620,848 | A * | 11/1986 | Sutherland .......... A61M 5/1456 128/DIG. 12 |
| 4,685,591 | A | 8/1987 | Schaefer et al. |
| 5,672,155 | A | 9/1997 | Riley et al. |
| 5,807,334 | A | 9/1998 | Hodosh et al. |
| 6,003,736 | A | 12/1999 | Ljunggren |
| 6,050,450 | A | 4/2000 | Gardos |
| 6,613,019 | B2 | 9/2003 | Munk |
| 7,678,084 | B2 | 3/2010 | Judson et al. |
| 7,794,429 | B2 | 9/2010 | Niehoff |
| 8,361,036 | B2 | 1/2013 | Moller et al. |
| 2002/0091358 | A1 | 7/2002 | Klitmose |
| 2004/0054326 | A1 | 3/2004 | Hommann et al. |
| 2006/0247578 | A1 | 11/2006 | Arguedas et al. |
| 2008/0200747 | A1* | 8/2008 | Wagner ............. A61M 5/14546 600/5 |
| 2010/0228121 | A1* | 9/2010 | Kazuhiro .......... A61M 5/14546 600/432 |

(Continued)

FOREIGN PATENT DOCUMENTS

WO   WO2005072795   8/2005

OTHER PUBLICATIONS

International Search Report and Written Opinion dated Jul. 30, 2019 re Int'l Application No. PCT/US19/25084. 14 pages.

*Primary Examiner* — Nathan R Price
*Assistant Examiner* — Tasnim Mehjabin Ahmed
(74) *Attorney, Agent, or Firm* — Silicon Edge Law Group LLP; Arthur J. Behiel (57) ABSTRACT

A device for dispensing a controlled amount of a fluid from a syringe, the syringe having a plunger extending along a linear axis through a syringe flange and into a syringe barrel. The device includes a housing to accommodate at least a portion of the syringe, and a drive wheel attached to the housing to contact a side of the plunger, the housing to press the drive wheel into the side of the plunger between the syringe flange and an end of the plunger.

27 Claims, 7 Drawing Sheets

(56) References Cited

U.S. PATENT DOCUMENTS

| | | | |
|---|---|---|---|
| 2016/0067417 A1* | 3/2016 | Bayer | A61M 5/2033 604/208 |
| 2016/0114109 A1* | 4/2016 | Lavi | A61M 5/1452 604/82 |
| 2017/0080154 A1 | 3/2017 | Mudd et al. | |
| 2018/0228968 A1 | 8/2018 | Hochman et al. | |

* cited by examiner

| John Doe |  |
|---|---|
| Last Visit: 08-30-2018 | |

Ready to Connect

| Chemistry A | 0.025 | 40 |
|---|---|---|
| Chemistry B | 0.030 | 35 |
| Chemistry C | 0.035 | 30 |
| Chemistry D | 0.040 | 25 |
| Chemistry E | 0.045 | 20 |

*Fig.6*

| | | |
|---|---|---|
| Chemistry A | 0.025 | 40 |
| Chemistry B | 0.030 | 35 |
| Chemistry C | 0.035 | 30 |
| Chemistry D | 0.040 | 25 |
| Chemistry E | 0.045 | 20 |

Fig.7

| John Doe | |
|---|---|
| Last Visit: 08-30-2018 | |

CONNECTED!

| Chemistry A | 0.025 | 40 |
|---|---|---|
| Chemistry B | 0.030 | 35 |
| Chemistry C | 0.035 | 30 |
| Chemistry D | 0.040 | 25 |
| Chemistry E | 0.045 | 20 |

Fig.8

INJECTION DEVICE

CROSS-REFERENCE TO RELATED APPLICATIONS

Not applicable.

STATEMENT REGARDING FEDERALLY SPONSORED RESEARCH AND DEVELOPMENT

Not applicable.

BACKGROUND OF THE INVENTION

The invention relates to drug delivery devices and more particularly to a device for dispensing a controlled amount of a fluid medication.

Medications such as testosterone esters, methotrexate, cyanocobalamin (vitamin B12), dental anesthetics, and botulinum toxin are typically administered as a series of doses of predetermined volume using conventional syringes. For example, botulinum toxin injection is widely used for the treatment of facial wrinkles and consists of a series of injections into specific muscles of the face. Injection of the botulinum toxin into the affected muscles inhibits release of acetylcholine at the neuromuscular junction and causes localized relaxation that smoothes the overlying skin and reduces wrinkles. To ensure that facial asymmetry does not result from uneven dosing of the botulinum toxin, administration of accurate injection volumes is important. This accuracy is conventionally achieved by clinicians through practice to develop consistent technique. Further, and considering the high cost of the botulinum toxin (a typical dose of Botox® Cosmetic consisting of 4 units per 0.1 ml costs a patient on average $40-$60), accurate administration of the botulinum toxin provides financial savings to the clinician as waste is reduced.

Injection devices adapted to deliver a controlled dose of a fluid medication may include electro-mechanical components operable to engage a plunger of a syringe or fluid compartment containing the medication. Such components include drive screws and movable drive elements. Typically these devices are bulky and cumbersome to use.

SUMMARY OF THE INVENTION

The present invention provides a device and method for dispensing a controlled amount of a fluid medication from a syringe. The present invention also provides a device and method for drawing an amount of fluid back into a syringe barrel from a syringe needle following injection of the fluid medication.

According to an embodiment of the present invention, a device for dispensing a controlled amount of a fluid from a syringe having a plunger extending along a linear axis through a syringe flange and into a syringe barrel includes a housing to accommodate at least a portion of the syringe, and a rotary drive attached to the housing to contact a side of the plunger, the housing to press the rotary drive into the side of the plunger between the syringe flange and an end of the plunger.

According to another embodiment of the present invention, a device for dispensing a controlled amount of a fluid from a syringe having a plunger extending along a linear axis through a syringe flange and into a syringe barrel includes a housing for accommodating at least a portion of the syringe, a rotary drive coupled to a motor attached to the housing, the rotary drive to engage the plunger proximate a syringe flange and drive the plunger along the linear axis through the syringe barrel, a controller for controlling the operation of the motor, and an actuator for selectively actuating the controller.

According to another embodiment of the present invention, a device for dispensing a controlled amount of a fluid from a syringe having a plunger extending along a linear axis through a syringe flange and into a syringe barrel includes a housing to accommodate at least a portion of the syringe, a cutter gear attached to the housing to contact a side of the plunger, the cutter gear having a plurality of teeth and an axis of rotation orthogonal to the linear axis of the syringe, the housing to press the cutter gear teeth into the side of the plunger between the syringe flange and an end of the plunger, a button connected to the housing along a longitudinal axis of the housing opposite the end of the plunger, and a motor mechanically coupled to the cutter gear and a controller electrically coupled to the motor and the button, the controller to enable the motor to rotate the cutter gear responsive to a selection of the button, the controller including a processor to receive user input indicative of a controlled amount of fluid to be dispensed and to operate the motor to drive the cutter gear and thereby dispense the controlled amount of fluid from the syringe.

According to one aspect of the present invention, the device is compact and easy to use in administering a fluid medication from a syringe.

According to another aspect of the present invention, the device is a programmable device operable to receive and execute user-selected commands.

According to another aspect of the present invention, the device is a programmable device operable to dispense a user-selected dose of a fluid medication from a syringe.

According to another aspect of the present invention, the device is a programmable device operable to dispense a user-selected dose of a fluid medication from a syringe at a pre-determined rate.

According to another aspect of the present invention, a method for dispensing a controlled amount of fluid includes accommodating a syringe containing a volume of fluid in a device having a rotary drive engageable to a syringe plunger proximate a syringe flange, receiving user input indicative of a controlled amount of fluid to be dispensed from the syringe upon user actuation of the device, and driving the rotary drive to dispense the controlled amount of fluid from the syringe upon user actuation of the device.

According to another aspect of the present invention, the method for dispensing a controlled amount of fluid includes reversing the rotation of the rotary drive to draw an amount of fluid back into the syringe following driving the rotary drive to dispense the controlled amount of fluid from the syringe.

BRIEF DESCRIPTION OF THE DRAWINGS

The present invention will be described with reference to the accompanying drawings which are provided by way of illustration only and wherein.

Corresponding parts are marked with the same reference symbols in all figures.

DETAILED DESCRIPTION OF THE INVENTION

With reference to the FIGS. 1-5, a device generally designated 10 is shown. The device 10 is sized and configured to fit comfortably in the hand 200 of a user administering an injection using a syringe 60. The syringe 60 includes a plunger 66 extending along a linear axis through a syringe flange 64 and into a syringe barrel 62. The device 10 has a tapered profile and provides the user with a compact means of dispensing a controlled amount of fluid, such as a dose of a medicine, by injection using the index finger 202, the middle finger 204, and the thumb 206 of his or her hand 200 in a conventional manner.

The device 10 includes a programmable, computer-controlled device having a housing 12. The housing 12 includes a front section 14 and a back section 16 that define an interior chamber of the device 10. The interior chamber may accommodate components of the device 10. The housing 12 may include a top section 18 and a bottom section 20. The housing 12 preferably has an elongated, tapered profile with the top section 18 having a smaller width than that of the bottom section 20 to facilitate handling of the device 10 when in use. A button 90 coupled to a switch 92 is disposed at the housing top section 18 opposite an end 68 of the plunger 66 and along a longitudinal axis of the housing 12. Selection of the button 90 enables the user to actuate the device 10 using his or her thumb 206.

The housing 12 includes an elongated channel 40 formed along a longitudinal axis thereof and configured to accommodate a portion of the syringe 60. The syringe linear axis is substantially parallel to the longitudinal axis of the housing 12.

The channel 40 may extend from proximate the housing top section 18 and terminate at the housing bottom section 20 to provide an aperture 22 through which the syringe barrel 62 extends from the housing 12 when in use. The channel 40 is sized to accommodate the syringe 60 with the syringe plunger 66 in its extended position in relation to the syringe barrel 62. In its extended position, the end 68 of the plunger 66 is disposed proximate the housing top section 18 and opposite the button 90. A flange support 72 formed in a recessed section 70 of the housing front section 14 is sized and configured to receive a flange 64 of the syringe 60 and to prevent movement of the barrel 62 relative to the device 10 during use. The flange support 72 is formed transverse to the longitudinal axis of the housing 12.

The housing bottom section 20 also includes finger rests 24 and 26 formed opposite each other and in recessed relation to the aperture 22. The finger rests 24 and 26 may include a plurality of spaced-apart ribs 28 formed to provide a gripping surface for the user's index and middle fingers 202 and 204 when the device 10 is in use. Finger rests 24 and 26 may be disposed such each of two sides of the syringe 60 includes one of the finger rests.

Figure 1:
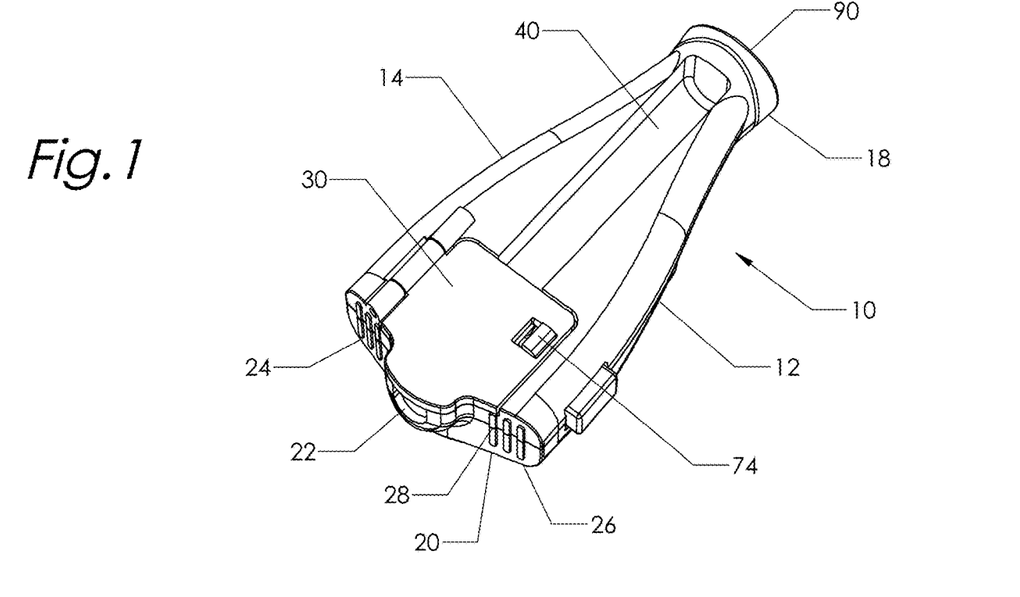
FIG. 1 is a perspective view of the device.
Figure 2:
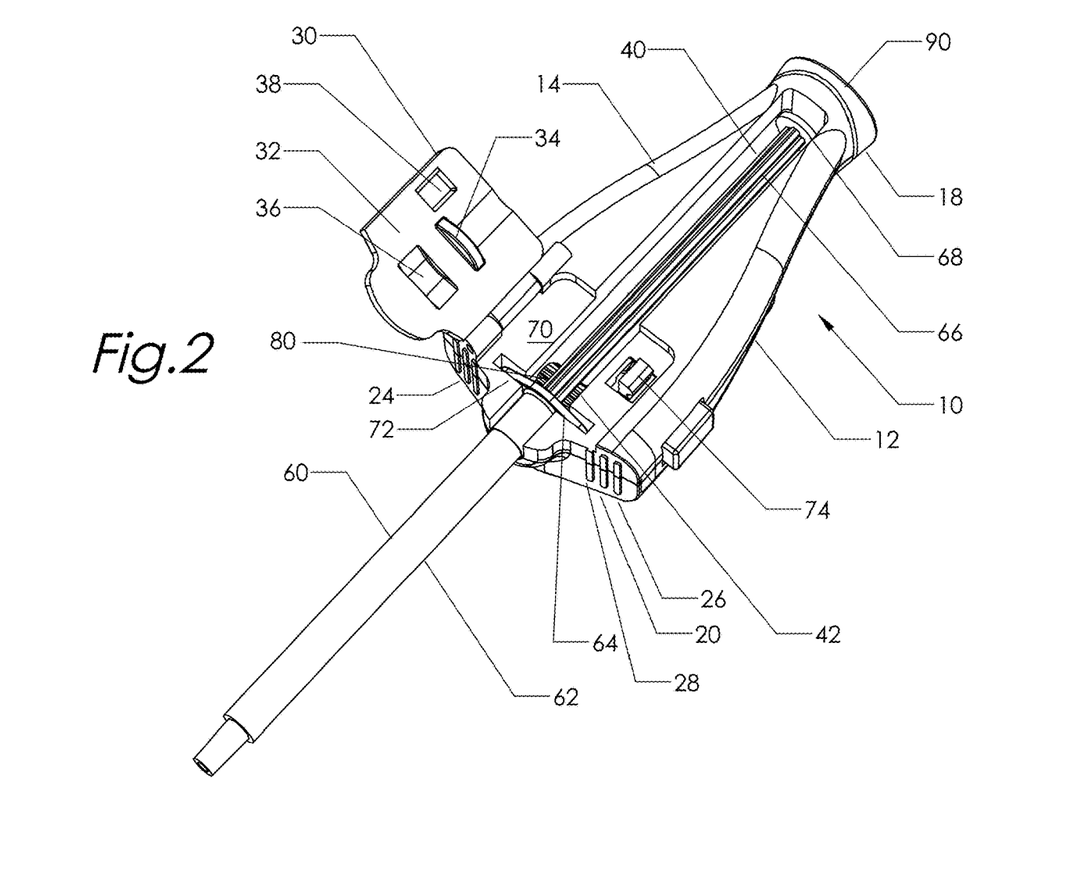
FIG. 2 is a perspective view of the device showing a syringe positioned therewithin.
Figure 3:
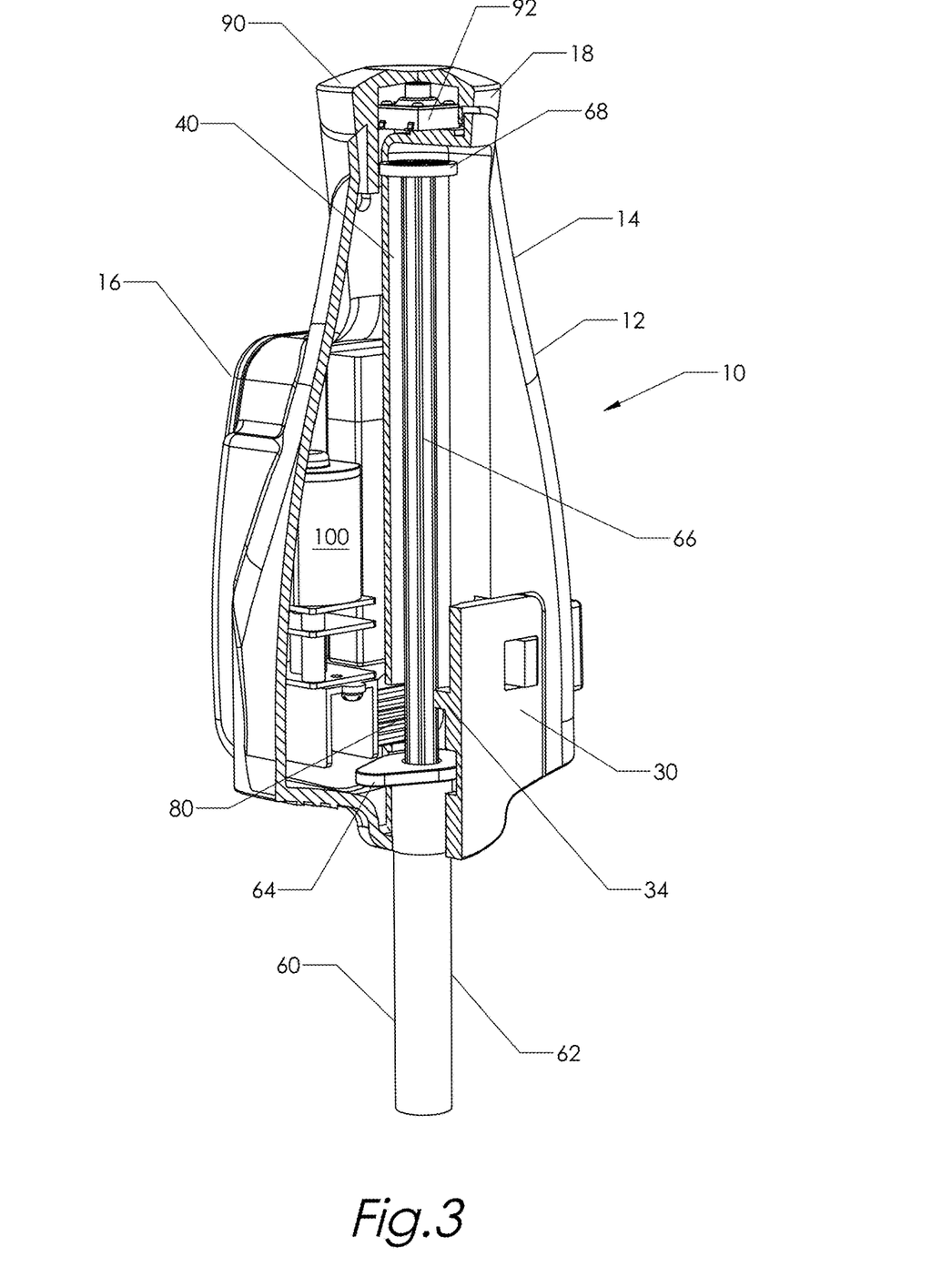
FIG. 3 is a perspective sectional view of the device showing a syringe plunger in an extended position.

In one aspect of the invention, the channel 40 may include an opening 42 formed proximate the flange support 72. A rotary drive having an axis of rotation orthogonal to the linear axis of the syringe 60 may be driven by a mechanically coupled electric motor 100 disposed in the interior chamber of the device 10. The rotary drive may comprise a cutter gear 80 having a plurality of teeth for cutting engagement with the plunger 66. The cutter gear 80 may extend partially through the opening 42 and contact a side of the plunger 66 proximate the syringe flange 64. Controlled actuation of the rotary drive is operable to rotate the cutter gear 80 causing the plurality of teeth to cut into the plunger 66 and displace the plunger 66 along the linear axis of the syringe to thereby dispense a controlled amount of fluid from the syringe barrel 62.

Figure 4:
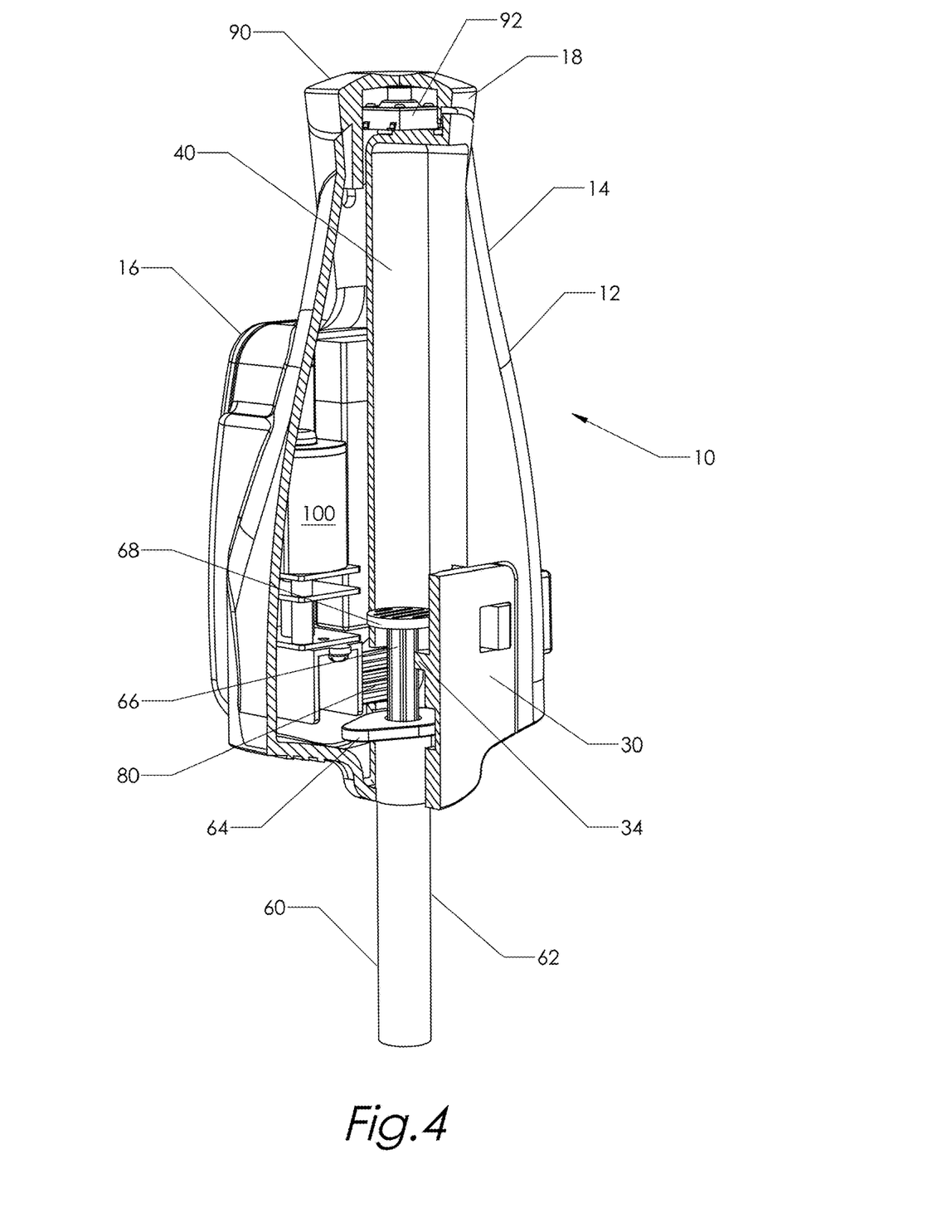
FIG. 4 is a perspective sectional view of the device showing the syringe plunger when it is fully inserted into a syringe barrel.
Figure 5:
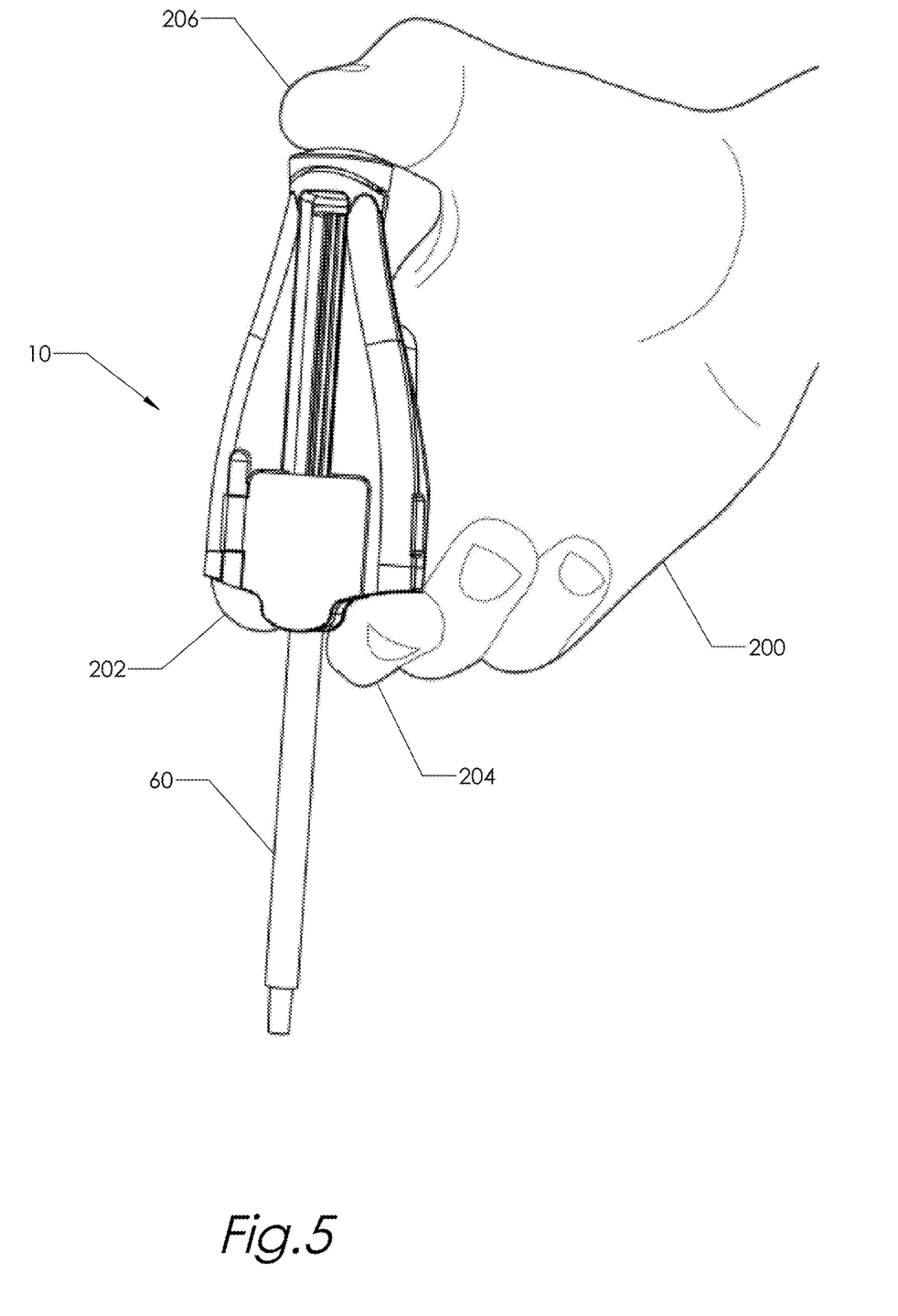
FIG. 5 is a perspective view of the device in use.

As shown in FIG. 4, when the plunger 66 is fully inserted into the syringe barrel 62 and the contents of the syringe barrel 62 have been dispensed, the end of the plunger 68 is proximate the flange 64 and the driver gear 80 is positioned between the end of the plunger 68 and the flange 64. By way of example, in the case of a conventional 1 cc syringe, the distance between the end of the plunger 68 and the syringe flange 64 when the plunger 66 is in its fully inserted position is approximately 9.75 mm. A cutter gear 80 having an outside diameter of 6.4 mm may be provided in this case to drive the plunger 66.

In other embodiments of the invention, the rotary drive may include a helical gear, a knurled gear, a knurled wheel, a textured wheel, a rubber wheel, a textured roller and a roller. In some embodiments of the invention, the rotary drive may have a frictional surface for engagement with a glass plunger.

A hinged door 30 may be positioned proximate the housing bottom section 20 and include an inside surface 32 having a catch 34 and a recessed section 36. The catch 34 is sized and positioned such that it contacts a second side of the plunger 66 to thereby press the plunger 66 against the rotary drive when the door 30 is in a closed position. The recessed section 36 is positioned such that it accommodates a portion of the flange 64 of the syringe 60 when the door 30 is in the closed position. A latch 74 is releasably engageable with a door catch 38 to secure the door 30 in the closed position.

In other embodiments of the invention, the plunger 66 may be pressed against the rotary drive by a bearing disposed on the door 30.

The device 10 includes a programmable controller electrically coupled to the rotary drive, the button 90, and the switch 92. The controller is operable to control the operation of the rotary drive in response to commands and signals received from a user. The controller may include a processor, a memory, a wireless transceiver, and I/O devices. The processor may include any type of logic circuit capable of executing instructions. The processor is configured to execute instructions for performing the operations and methods discussed herein. The memory may store information including sequences of executable program instructions that are executed by the processor. The controller may be disposed in the interior chamber of the device 10.

In one aspect of the invention, selection of the button 90 switches the switch 92 and actuates the controller to enable the motor to rotate the rotary drive. User selection of the button 90 may occur over a selection period and the controller may rotate the rotary drive a rotational amount independent of the selection period.

In another aspect of the invention, the controller reverses the rotary drive by a second rotational amount responsive to the selection of the button 90. The second rotational amount may be independent of the selection period.

The wireless transceiver can be a WiFi transceiver, an infrared transceiver, a Bluetooth transceiver, a WiMax transceiver, a wireless cellular telephony transceiver, or other radio frequency transceiver. The controller may be operable to receive information including user signals from a remote transceiver by means of the wireless transceiver. The remote transceiver may include a local control server, a remote Web application server, or a wireless electronic device such as a smartphone, smart watch, tablet or personal computer.

Figure 6:
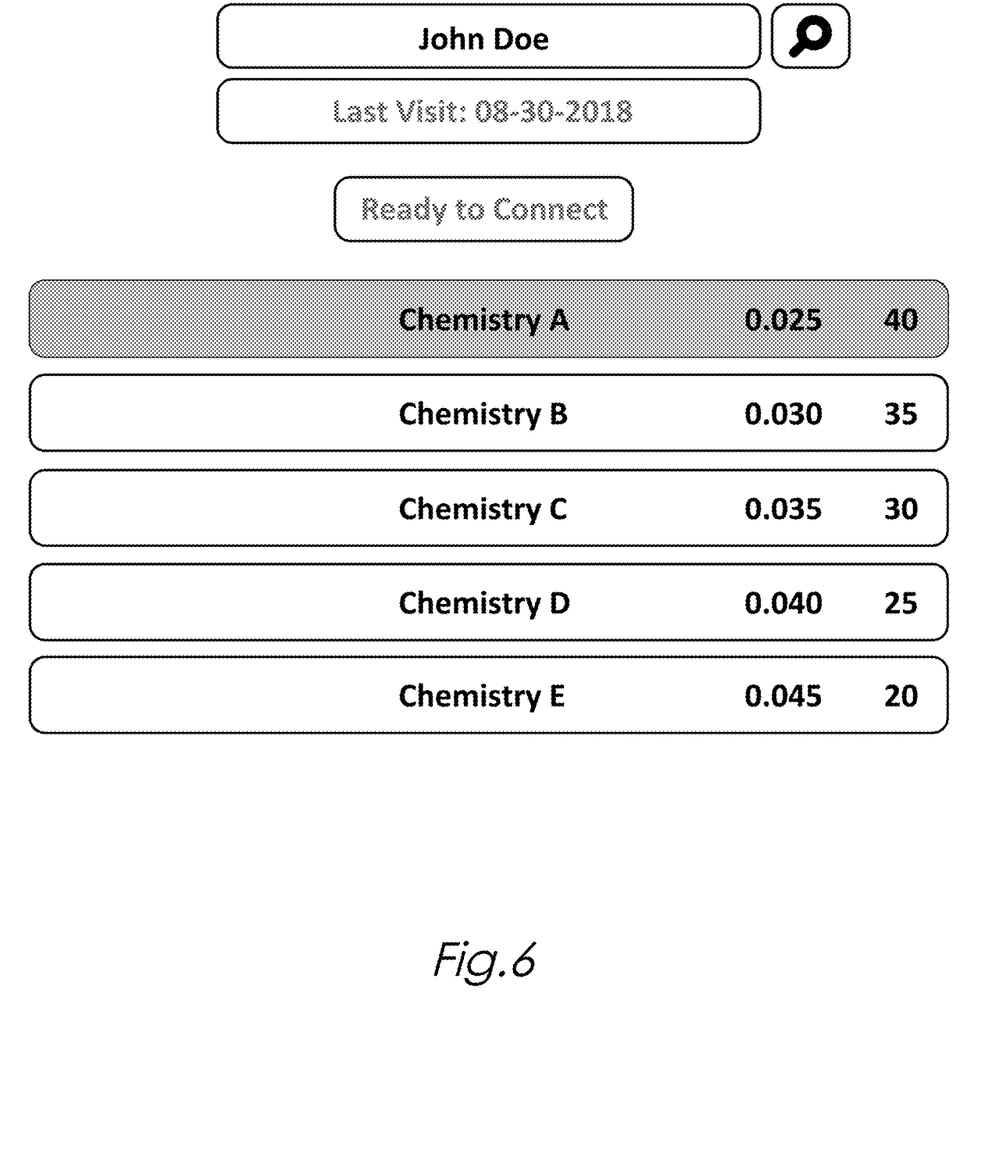
FIG. 6 is a screen shot of a device application user interface showing a selection screen.
Figure 7:
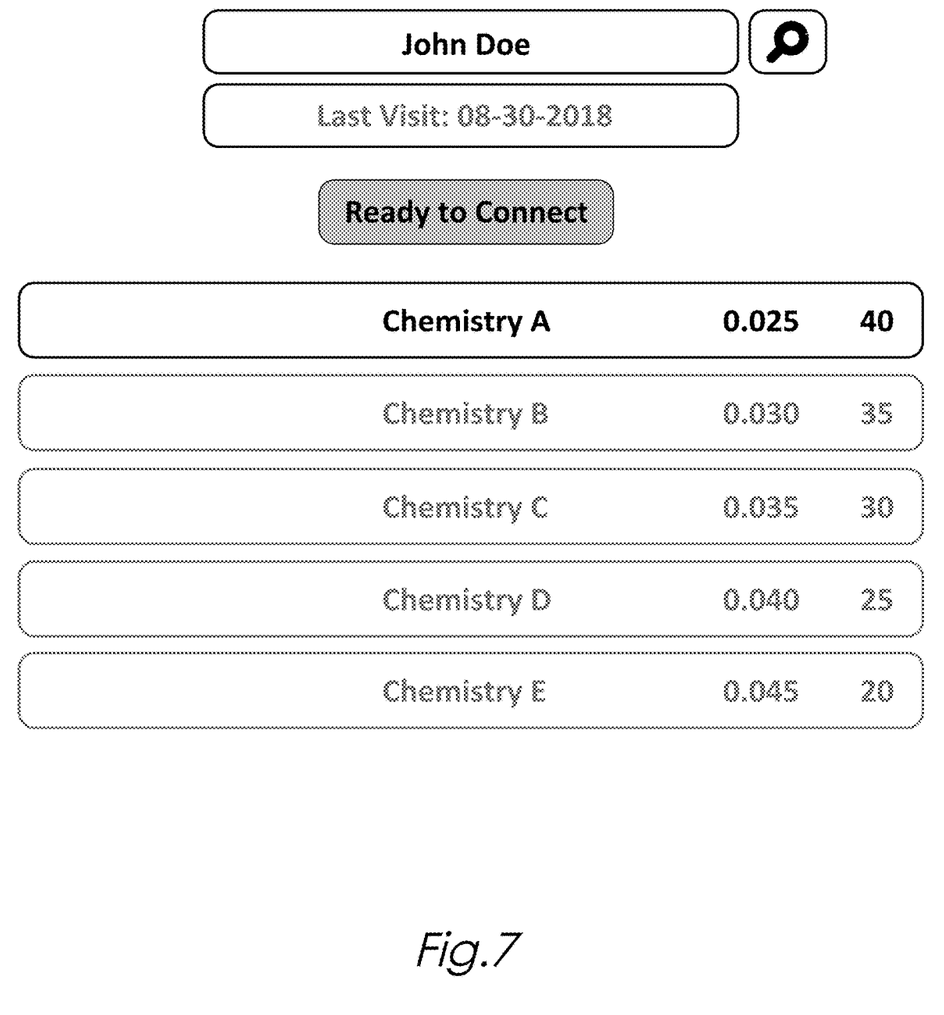
FIG. 7 is a screen shot of a device application user interface showing user selected chemistry and dose amounts.
Figure 8:
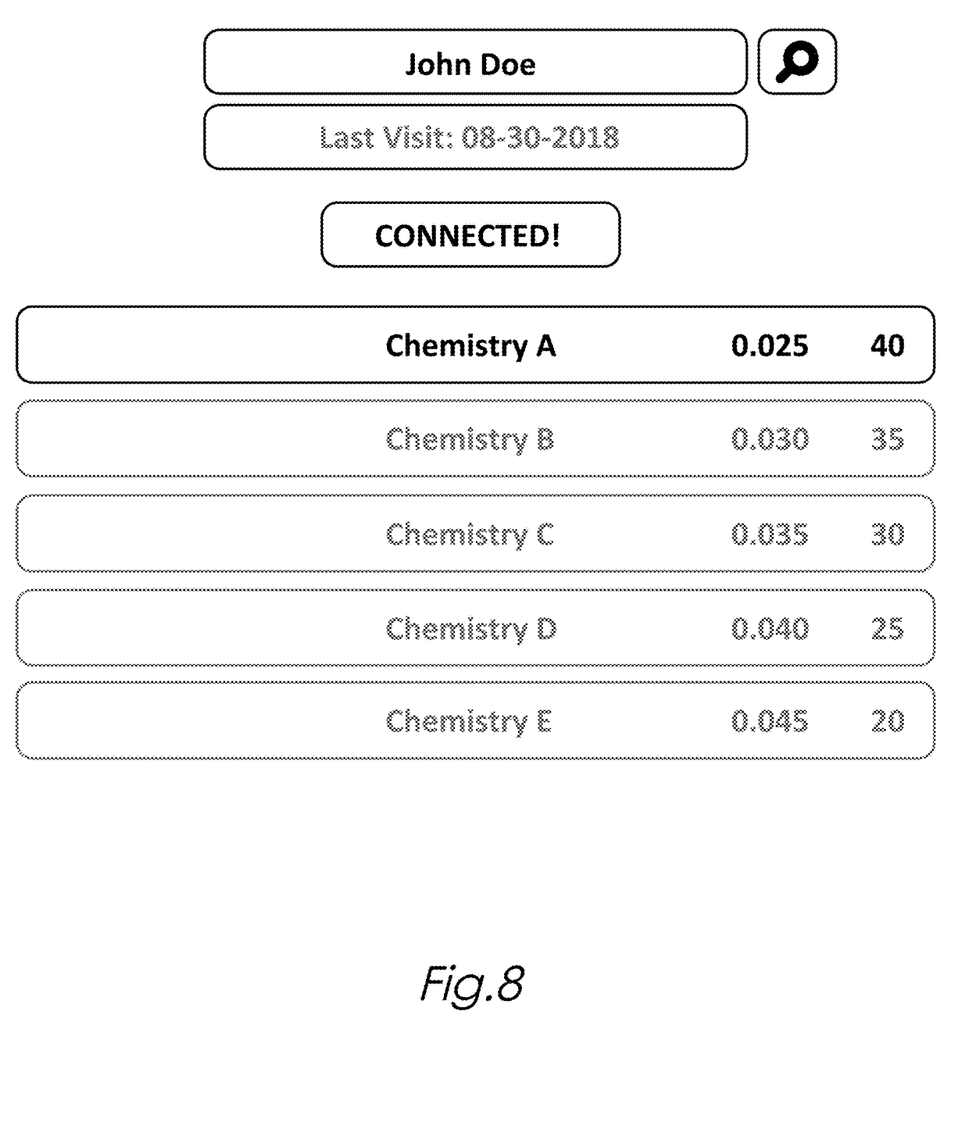
FIG. 8 is a screen shot of a device application user interface showing connection to the controller of the device.

With reference to FIGS. 6-8, exemplary screen shots of a remote application user interface displayed by a remote receiver such as a tablet show a means by which a user selects the amount of liquid medication to be dispensed with each actuation of the device 10. The remote application may be coupled to a memory for storing patient identifying information as well as the date of the patient's last visit, the chemistry last selected, the last dosage selected, and indicia of rotational amounts.

The remote application may provide the user with a menu of chemistries from which to select. In the case where the syringe 60 being used is a 1 cc syringe, user selection of "Chemistry A" indicates that each of 40 doses to be dispensed will have a volume of 0.025 ml. Following user selection of a desired chemistry and dosage, the remote receiver may send a signal to the controller of the device 10 following user selection of the "Ready to Connect" button. The controller may provide the remote application with confirmation of receipt of the signal by means of a "Connected" button. The button 90 may then be selected to operate the device 10.

In some embodiments of the invention, the controller of the device 10 is operable to prevent actuation of the device 10 when the device 10 is not connected to the remote application. In other embodiments, the controller of the device 10 is operable to control the motor 100 to dispense a selected chemistry at a preset rate. In yet other embodiments, the controller of the device 10 is operable to control the torque of the motor 100.

The controller may implement a method in which a signal is received indicating the amount of liquid to be dispensed from the syringe barrel 62 with each user actuation of the device 10. The controller may also implement a method in which the rotary drive is driven in reverse following the dispensing of a dose in order to draw the plunger 66 from the syringe barrel 62 to thereby draw the drop of fluid that may form following the injection back into the needle of the syringe 60. The drop of fluid may have a volume between 0.001 ml and 0.005 ml. The controller may include a Wheatstone bridge circuit operable to reverse the polarity of a motor drive voltage. A rotary encoder coupled to the shaft of the motor 100 may provide information to the controller with respect to the motion of the rotary drive.

Specific details are given in the description to provide a thorough understanding of the embodiments. However, it will be understood by one of ordinary skill in the art that the embodiments may be practiced without these specific details. For example, the elongated channel is shown as being formed in the front section of the housing of the device but could be formed in the back section. Further, well-known processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention.

Having described several embodiments, it will be recognized by those of skill in the art that various modifications, alternatives constructions and equivalents may be used without departing from the spirit of the invention. Accordingly, the above description should not be taken as limiting the scope of the invention.

The invention claimed is:

1. A system comprising:
a syringe, the syringe comprising a plunger extending along a linear axis through a syringe flange and into a syringe barrel; and
a device for dispensing a controlled amount of a fluid from the syringe, the device comprising:
a housing to accommodate at least a portion of the syringe, and a rotary drive attached to the housing to contact a side of the plunger, the housing configured to press the rotary drive into the side of the plunger between the syringe flange and an end of the plunger, wherein the rotary drive comprises teeth that engage and drive the plunger by cutting into the side of the plunger; and
a button, configured to actuate the device to dispense the controlled amount of the fluid from the syringe, connected to the housing along a longitudinal axis thereof and opposite the end of the plunger.

2. The system of claim 1, wherein the rotary drive has an axis of rotation orthogonal to the linear axis.

3. The system of claim 1, wherein the rotary drive is disposed against the plunger and between the syringe flange and the end of the plunger when the plunger is fully inserted into the syringe barrel.

4. The system of claim 1, further comprising a motor mechanically coupled to the rotary drive and a controller electrically coupled to the motor and the button, the controller to enable the motor to rotate the rotary drive responsive to a selection of the button.

5. The system of claim 4, wherein the selection of the button occurs over a selection period and the controller rotates the rotary drive a rotational amount independent of the selection period.

6. The system of claim 5, further comprising memory communicatively coupled to the controller, the memory to store indicia of the rotational amount.

7. The system of claim 5, wherein the controller reverses the rotary drive by a second rotational amount responsive to the selection of the button.

8. The system of claim 7, wherein the second rotational amount is independent of the selection period.

9. The system of claim 1, the housing further comprising a bottom section opposite the button, the bottom section including finger rests, one finger rest on each of two sides of the syringe.

10. The system of claim 9, the housing further comprising a flange support to accept the syringe flange, the flange support disposed transverse to the longitudinal axis.

11. The system of claim 1, the housing including a channel to accommodate the at least a portion of the syringe, the channel including an opening through which the rotary drive contacts the side of the plunger.

12. The system of claim 11, further comprising a catch to selectively secure the syringe in the housing.

13. The system of claim 12, the catch to press against a second side of the plunger in order to press the plunger against the rotary drive.

14. The system of claim 13, the catch including a bearing surface in contact with the second side of the plunger opposite the side of the plunger in contact with the rotary drive.

15. A system comprising:
- a syringe, the syringe comprising a plunger extending along a linear axis through a syringe flange and into a syringe barrel; and
  - a device for dispensing a controlled amount of a fluid from the syringe, the device comprising:
  - a housing for accommodating at least a portion of the syringe, a rotary drive coupled to a motor attached to the housing, the rotary drive comprising teeth that engage the plunger proximate the syringe flange and drive the plunger along the linear axis through the syringe barrel;
  - a button, configured to actuate the device to dispense the controlled amount of the fluid from the syringe, connected to the housing along a longitudinal axis thereof and opposite an end of the plunger; and
  - a controller for controlling the operation of the motor.

16. The system of claim 15, wherein the rotary drive engages the syringe plunger between the syringe flange and an end of the plunger when the syringe plunger is fully inserted into the syringe barrel.

17. The system of claim 15, wherein the rotary drive has an axis of rotation orthogonal to the linear axis of the syringe.

18. The system of claim 15, wherein the rotary drive comprises a gear.

19. The system of claim 15, wherein the rotary drive comprises a wheel.

20. The system of claim 15, wherein the controller further comprises a processor to receive user input indicative of a controlled amount of fluid to be dispensed and to operate the motor to drive the rotary drive and thereby dispense the controlled amount of fluid from the syringe upon actuation thereof.

21. The system of claim 15, wherein the housing further comprises a front section and a back section, the front and back sections tapering from a first width at bottom portions thereof to a lesser second width at top portions thereof.

22. The system of claim 15, wherein the housing further comprises a bottom section, the bottom section including spaced-apart recessed portions having a plurality of ribs formed thereon.

23. The system of claim 15, wherein the housing comprises a door having a catch on an inside surface thereof, the catch sized and configured to contact the syringe plunger and press the syringe plunger against the rotary drive when the door is closed.

24. The system of claim 15, the housing further comprising a flange support to accept the syringe flange, the flange support disposed transverse to a longitudinal axis of the housing.

25. A method for dispensing a controlled amount of fluid comprising:
   (a) providing the system of claim 1;
   (b) accommodating the syringe of the system containing a volume of fluid in the device of the system;
   (c) receiving user input indicative of a controlled amount of fluid to be dispensed from the syringe upon user actuation of the device; and
   (d) driving the rotary drive to dispense the controlled amount of fluid from the syringe upon user actuation of the device.

26. The method of claim 25, further comprising reversing the rotation of the rotary drive to draw an amount of fluid back into the syringe following driving the rotary drive to dispense a controlled amount of fluid from the syringe.

27. A system comprising:
- a syringe, the syringe comprising a plunger extending along a linear axis through a syringe flange and into a syringe barrel; and
  - a device for dispensing a controlled amount of a fluid from the syringe, the device comprising:
  - a housing to accommodate at least a portion of the syringe, a cutter gear attached to the housing to contact a side of the plunger, the cutter gear comprising a plurality of teeth that engage and drive the plunger by cutting into the side of the plunger and an axis of rotation orthogonal to the linear axis of the syringe, the housing configured to press the cutter gear teeth into the side of the plunger between the syringe flange and an end of the plunger;
  - a button, configured to actuate the device to dispense the controlled amount of the fluid from the syringe, connected to the housing along a longitudinal axis of the housing and opposite the end of the plunger; and
  - a motor mechanically coupled to the cutter gear and a controller electrically coupled to the motor and the button, the controller to enable the motor to rotate the cutter gear responsive to a selection of the button, the controller including a processor to receive user input indicative of a controlled amount of fluid to be dispensed and to operate the motor to drive the cutter gear and thereby dispense the controlled amount of fluid from the syringe.

* * * * *